United States Patent [19]

Brittain et al.

[11] 4,386,100
[45] May 31, 1983

[54] SPIRO [IMIDAZOLIDINE 4,3'-INDOLINE]2,2',5-TRIONES, COMPOSITIONS AND USE

[75] Inventors: David R. Brittain, Macclesfield; Robin Wood, Hazel Grove, both of England

[73] Assignee: Imperial Chemical Industries PLC, London, England

[21] Appl. No.: 377,134

[22] Filed: May 11, 1982

[30] Foreign Application Priority Data

May 12, 1981 [GB] United Kingdom ............... 8114399

[51] Int. Cl.³ ............... C07D 487/10; A61K 31/415
[52] U.S. Cl. ............................ 424/273 R; 542/445; 548/309
[58] Field of Search .............. 542/445; 548/309; 424/273 R

[56] References Cited

U.S. PATENT DOCUMENTS 4,117,230 9/1978 Sarges et al. ............... 548/309

FOREIGN PATENT DOCUMENTS 50-137976 11/1975 Japan.

OTHER PUBLICATIONS

Otomasu et al., *Chem. Pharm. Bull.* (1975) vol. 23, pp. 1431–1435.

*Primary Examiner*—Robert Ramsuer
*Attorney, Agent, or Firm*—Cushman, Darby & Cushman

[57] ABSTRACT

The invention provides novel non-toxic biodegradable derivatives of the formula:

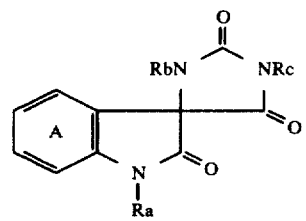

wherein Ra is (1–12C)alkyl, phenyl, naphthylmethyl or cinnamyl, the aromatic rings of which optionally bear one or two halogeno substituents, or Ra is benzyl optionally bearing up to 3 substituents independently selected from halogeno, trifluoromethyl, (1–4C)alkyl, (1–4C)alkoxy, nitro, cyano and hydroxy; Rb and Rc are independently selected from hydrogen and non-toxic biodegradable protecting radicals, but are not both hydrogen; and benzene ring A optionally bears one substituent selected from halogeno, (1–4C)alkyl, (1–4C)alkoxy, nitro and hydroxy, or bears two substituents independently selected from halogeno, (1–4C)alkyl and nitro; pharmaceutical compositions thereof; and processes for their manufacture.

The amides of formula I in which Rb=Rc=H are potent inhibitors of the enzyme aldose reductase. The derivatives of formula I provided by the invention are of use in vivo in the treatment or prophylaxis of certain complications of diabetes or galactosemia.

12 Claims, No Drawings

SPIRO [IMIDAZOLIDINE 4,3'-INDOLINE]2,2',5-TRIONES, COMPOSITIONS AND USE

This invention concerns novel amide derivatives, and more particularly it concerns novel non-toxic biodegradable derivatives of 1'-substituted spiro[imidazolidine-4,3'-indoline]-2,2',5-triones, which possess the property of inhibiting the enzyme aldose reductase in vivo. The invention also concerns processes for the manufacture of the said derivatives, pharmaceutical compositions thereof and a method for use thereof in the treatment or prophylaxis of certain complications of protracted diabetes or galactosemia.

The enzyme aldose reductase is responsible for the catalytic conversion of aldoses, for example glucose and galactose, to the corresponding alditols, for example sorbitol and galactitol respectively. Alditols penetrate cell membranes poorly and, once formed, tend to be removed only by further metabolism. As a consequence, alditols tend to accumulate within cells where they are formed, causing a rise in internal osmotic pressure which may in turn be sufficient to destroy or impair the function of the cells themselves. In addition, raised alditol levels may result in abnormal levels of their metabolites which may themselves impair or damage cellular function. However, the enzyme aldose reductase has a relatively low substrate affinity, that is, it is only effective in the presence of relatively large concentrations of aldose. Such large concentrations of aldose are present in the clinical conditions of diabetes (excessive glucose) and galactosemia (excessive galactose). As a consequence, inhibitors of the enzyme aldose reductase are useful in the reduction or prevention of the development of those complications of protracted diabetes or galactosemia which may be due in part to the accumulation of sorbitol or galactitol respectively. Such complications are, for example, macular oedema, cataract, retinopathy or impaired neural conduction.

It is known that certain spiro-linked hydantoins (spiro-linked imidazolidine-2,5-diones) derived from various bicyclic ketones are inhibitors of the enzyme aldose reductase, for example the compounds of the general formula:

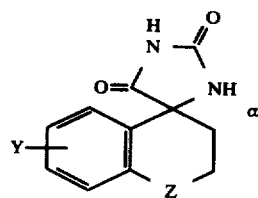

wherein Z is oxygen, sulphur, sulphinyl, sulphonyl, methylene or a direct bond, and Y stands for various optional substituents, described by Sarges in U.S. Pat. No. 4,117,230. We have now discovered that certain derivatives of novel spiro-linked hydantoins having the formula I below and derived from 1-substituted-indoline-2,3-diones possess potent aldose reductase inhibitory properties in vivo and this is the basis of our invention. This discovery is surprising in view of the various chemical differences involved, for example in view of the presence of an amidic carbonyl radical in the α-position relative to the spiro-carbon atom, which position is always occupied by a methylene radical in the aldose reductase inhibitory spiro-hydantoins of the prior art.

Certain related spiro-hydantoins derived from 1-substituted-indoline-2,3-diones are known. In particular, 1'-methyl, 1'-allyl- and 1'-benzyl-spiro[imidazolidine-4,3'-indoline]-2,2',5-trione have been described by Otomasu et alia in *Chem.Pharm.Bull.*, 1975, 23, 1431-1435, but no pharmacological properties have been ascribed to them.

According to the invention there is provided a non-toxic biodegradable derivative of a 1'-substituted-spiro[imidazolidine-4,3'-indoline]-2,2',5-trione, said derivative having the formula:

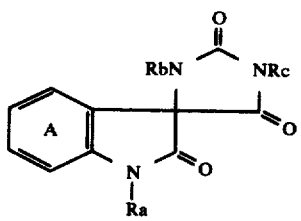

wherein Ra is a (1-12C)alkyl radical, a phenyl, naphthylmethyl or cinnamyl radical, the aromatic rings of which optionally bear one or two halogeno radicals, or Ra is a benzyl radical optionally bearing one, two or three substituents independently selected from halogeno, trifluoromethyl, (1-4C)alkyl, (1-4C)alkoxy, nitro, cyano, and hydroxy radicals; Rb and Rc are independently selected from hydrogen and non-toxic biodegradable protecting radicals, but are not both hydrogen; and benzene ring A optionally bears one substituent selected from halogeno, (1-4C)alkyl, (1-4C)alkoxy, nitro and hydroxy radicals, or bears two substituents independently selected from halogeno, (1-4C)alkyl and nitro radicals.

The compounds of formula I are derivatives of spiro[imidazolidine-4,3'-indoline] which is numbered as follows:

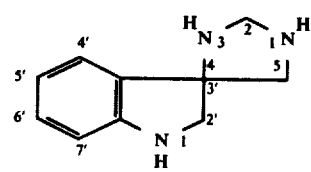

This numbering system will be used throughout the present specification. The symbols Ra, Rb, Rc et cetera are used to depict generic radicals in this specification and have no other significance.

The compounds of formula I possess at least one asymmetric carbon atom, namely the spiro-linked carbon atom. They therefore exist, and may be isolated, in racemic and optically-active forms. This invention relates to the racemic form of a compound of formula I or to any optically-active form which possesses aldose reductase inhibitory properties, it being well known in the art how to prepare optically active forms, for example by synthesis from optically-active starting materials, and how to determine the aldose reductase inhibitory properties by the standard tests described herein below.

A particular value for Ra when it is a (1-12C) alkyl radical is, for example, a methyl, ethyl, propyl, butyl, pentyl, hexyl, nonyl or decyl radical.

Particular values for substituents which may be present on benzene ring A or on an aryl moiety in Ra as defined above are, by way of example only:

for a halogeno, a fluoro, chloro, bromo or iodo radical;

for a (1–4C)alkyl, a methyl or ethyl radical; and for a (1–4C)alkoxy radical, a methoxy or ethoxy radical.

Particular values for ring A are when it is unsubstituted or bears 4'-chloro, 5'-fluoro, 5'-chloro, 5'-bromo, 5'-methyl, 5'-methoxy, 5'-hydroxy, 5'-nitro, 6'-chloro, 7'-fluoro, 7'-chloro, 7'-methyl, 7'-ethyl, 5',6'-difluoro, 5',6'-dichloro, 4',5'-dichloro, 5',6'-dimethyl, 5'-bromo-7'-nitro or 5'-chloro-7'-methyl substituents.

Particular values for Ra are when it is a methyl, n-propyl, n-hexyl, n-nonyl, n-decyl, phenyl, cinnamyl, 3,4-dichlorocinnamyl, naphth-1-ylmethyl, naphth-2-ylmethyl, benzyl, 3,4-dichlorobenzyl, 4-bromo-2-fluorobenzyl, 4-methylbenzyl, 2-fluoro-4-iodobenzyl, 4-bromo-3-chlorobenzyl, 4-chlorobenzyl, 4-bromobenzyl, 3,4-dimethoxybenzyl, 3-(trifluoromethyl)benzyl, 2-cyanobenzyl, 4-cyanobenzyl, 4-bromo-2-fluoro-5-nitrobenzyl, 4-nitrobenzyl, 4-bromo-3,5-dichlorobenzyl, 2,4-dichlorobenzyl, 4-hydroxybenzyl or 3,5-dichlorobenzyl radical.

A preferred value for ring A is when it is unsubstituted or bears a halogeno substituent, for example a chloro substituent and especially such a substituent located at position 5', 6' or 7'.

A preferred value for Ra is when it is a benzyl radical bearing one or two halogeno radicals, for example when it is a 4-halogeno-, 2,4-dihalogeno-, 3,4-dihalogeno- or 3,5-dihalogeno-benzyl radical, such as a 4-bromo-, 4-bromo-2-fluoro, 2-fluoro-4-iodo-, 3,4-dichloro-, 4-bromo-3-chloro- or 3,5-dichloro-benzyl radical.

As stated hereinbefore, the derivatives of the 1'-substituted-spiro[imidazolidine-4,3'-indoline]-2,2',5-triones of formula I possess potent aldose reductase inhibitory properties in vivo. However, they are not in general particularly active in vitro, that is outside the animal being treated, but act principally by virtue of the removal in vivo of the biodegradable radicals Rb and/or Rc to give the compounds of formula I in which Rb and Rc are both hydrogen, which compounds are themselves active as aldose reductase inhibitors (and are hereinafter referred to as "the inhibitors") both in vitro as well as in vivo.

It follows, therefore, that the nature of the biodegradable radicals Rb and Rc is critical only to the adsorption transport and ultimate release of the inhibitors in the tissue containing the aldose reductase enzyme which is to be inhibited. By suitable choice of biodegradable protecting radical, based on their generally known rate of enzymic degradation, it is possible to produce derivatives according to the invention which result in a delayed or sustained release of the inhibitors in vivo and which have modified bioabsorption and distribution properties. The invention therefore embraces a wide variety of non-toxic biodegradable protecting radicals for Rb and Rc. The term "non-toxic biodegradable protecting radical" includes any of the radicals in the known chemical art which are capable of being attached to the nitrogen atoms of the hydantoin ring, are not inherently toxic, and yet which are capable of removal in vivo, for example by enzymic degradation, to liberate the inhibitor in sufficient quantity to inhibit the enzyme aldose reductase, and do not give rise to toxic by-products.

Accordingly, particular values for Rb and/or Rc when they are other than hydrogen are, for example:

(i) an acyl or 1-(acyloxy)alkyl radical (especially a 1-(acyloxy)-(1–6C)alkyl radical), in either of which the acyl stands for: an alkanoyl radical (especially a (2–20-C)alkanoyl radical), an optionally substituted aroyl radical, an alkoxycarbonyl radical (especially a (1–10C)alkoxycarbonyl radical), an optionally substituted aralkoxycarbonyl radical (especially an optionally substituted benzyloxycarbonyl radical), or an alkoxyoxalyl radical (especially a [(1–10C)alkoxy]oxalyl radical);

(ii) an N-alkylcarbamoyl (especially an N-(1–6C)alkylcarbamoyl), N,N-di-alkylcarbamoyl (especially an N,N-di-(1–6C)alkylcarbamoyl)radical, or an optionally substituted N-aryl or N-aralkylcarbamoyl radical; or (iii) an optionally substituted phthalidyl radical.

Specific values for Rb and/or Rc in any of the above categories are, for example, as follows:

(i) for (2–12C)alkanoyl, an acetyl, pivaloyl, butyryl or stearoyl radical;

for optionally substituted aroyl, a benzoyl, methylbenzoyl, chlorobenzoyl or cyanobenzoyl radical;

for (1–10C)alkoxycarbonyl, an ethoxycarbonyl or t-butoxycarbonyl radical;

for optionally substituted benzyloxycarbonyl, a benzyloxycarbonyl or 4-chlorobenzyloxycarbonyl radical;

for 1-[(2–20C)alkanoyl]oxy(1–6C)alkyl, a pivaloyloxymethyl, stearoyloxymethyl or 1-(pivaloyloxy)ethyl radical;

for [(1–10)alkoxy]oxalyl, an ethoxyoxalyl or methoxyoxalyl radical;

for 1-(optionally substituted aroyloxy)-(1–6C)alkyl, a benzoyloxymethyl, (chlorobenzoyl)oxymethyl, (methylbenzoyl)oxymethyl, (methoxybenzoyl)oxymethyl or (cyanobenzoyl)oxymethyl radical; and for 1-[(1–10C)alkoxycarbonyloxy]-(1–6C)alkyl, an (ethoxycarbonyl)oxymethyl or 1-(ethoxycarbonyloxy)ethyl radical;

(ii) for N-(1–6C)alkylcarbamoyl, an N-methylcarbamoyl radical;

for N,N-di-(1–6C)alkylcarbamoyl, an N,N-dimethylcarbamoyl radical; and for optionally substituted N-aryl or N-aralkylcarbamoyl, an N-phenylcarbamoyl, N-(methoxyphenyl)carbamoyl, N-benzylcarbamoyl or N-(methylbenzyl)carbamoyl radical; and (iii) for optionally substituted phthalidyl, a phthalidyl radical optionally bearing an alkyl, alkoxy or halogeno radical, such as a fluoro, chloro, bromo, methyl or methoxy radical.

The particular values for Rb and Rc selected will, however, necessarily vary with the required rate of biodegradation, for example relatively slow release of the inhibitor in vivo may be required. However, this rate can readily be determined by routine procedures well known in the art.

Particular groups of derivatives of the invention are comprised by the following compounds of formula I defined hereinbefore wherein:

(a) Ra is a (1–12C)alkyl or an unsubstituted benzyl radical; and benzene ring A bears at least one halogeno substituent;

(b) Ra is a phenyl, cinnamyl or naphthylmethyl radical the aromatic rings of which optionally bear one or two halogeno radicals; and benzene ring A is unsubstituted or bears at least one halogeno substituent; and (c) Ra is a benzyl radical bearing one, two or three substituents independently selected from halogeno, trifluoromethyl, cyano, hydroxy, nitro, methyl and methoxy radicals; and benzene ring A is unsubstituted or bears one or two substituents as defined hereinbefore; and, in each group, Rb and Rc have the meanings defined hereinbefore.

A group of preferred derivatives of the invention comprises those compounds of formula I wherein Ra is a 3,4-dichlorobenzyl, 4-bromo-2-fluorobenzyl, 4-bromo-3-chlorobenzyl or 2-fluoro-4-iodobenzyl radical and benzene ring A is unsubstituted or bears 5'-fluoro, 5'-chloro, 5'-bromo, 5',6'-difluoro or 5',6'-dichloro substituents; Rb is hydrogen or an alkoxycarbonyl, aralkoxycarbonyl, alkoxyoxalyl or a 1-[alkoxycarbonyloxy]alkyl radical; and Rc has any of the meanings defined hereinbefore.

Non-toxic biodegradable derivatives of the following aldose reductase inhibitors are of special interest:

1'-(3,4-dichlorobenzyl)-spiro[imidazolidine-4,3'-indoline]-2,2',5-trione,

1'-(4-bromo-2-fluorobenzyl)-spiro[imidazolidine-4,3'-indoline]-2,2',5-trione,

1'-(3,4-dichlorobenzyl)-5'-fluorospiro[imidazolidine-4,3'-indoline]-2,2',5-trione, 1'-(4-bromo-3-chlorobenzyl)-spiro[imidazolidine-4,3'-indoline]-2,2',5-trione, 5'-chloro-1'-(3,4-dichlorobenzyl)spiro[imidazolidine-4,3'-indoline]-2,2',5-trione, 1'-(4-bromo-2-fluorobenzyl)-5'-chloro-spiro[imidazolidine-4,3'-indoline]-2,2'-5-trione, 5'-bromo-1'-(3,4-dichlorobenzyl)-spiro[imidazolidine-4,3'-indoline]-2,2',5-trione, 1'-(4-bromo-2-fluorobenzyl)-5'-fluoro-spiro[imidazolidine-4,3'-indoline]-2,2',5-trione, 1'-(3,4-dichlorobenzyl)-5',6'-dichloro-spiro[imidazolidine-4,3'-indoline]-2,2',5-trione, 1'-(3,4-dichlorobenzyl)-5',6'-difluoro-spiro[imidazolidine-4,3'-indoline]-2,2',5-trione and 1'-(2-fluoro-4-iodobenzyl)-spiro[imidazolidine-4,3'-indoline]-2,2',5-trione.

A particular group of derivatives of the invention which are especially preferred comprises those derivatives of formula I wherein Ra and Rc have any of the aforementioned general, particular or preferred values and Rb is hydrogen.

Particular derivatives of formula I are provided in accompanying Examples. Of these the derivatives described in Examples 1, 15 and 16 are of special interest.

The derivatives of the invention may be manufactured by any general procedure known in the art to be applicable to the preparation of analogous derivatives. Such procedures are provided as a further feature of the invention and are illustrated by the following in which Ra, Rb, Rc and benzene ring A have the meanings defined above:

(a) For a derivative of formula I wherein Rb and/or Rc is other than an alkyl- or aralkylcarbamoyl radical, hereafter referred to as L, reacting a compound of formula I wherein Rb and/or Rc is hydrogen with a compound of the formula L.Z wherein L has the meanings defined above and Z is a suitable leaving group.

Particular examples of L.Z suitable for incorporating a range of L radicals are, for example, a (2-20C)alkanoyl chloride or bromide such as acetyl, pivaloyl or stearoyl chloride or bromide, a (2-20C)alkanoic acid anhydride such as acetic or propionic anhydride, a (1-10C)alkyl chloroformate such as ethyl or methyl chloroformate, an aralkyl chloroformate such as benzyl chloroformate, an alkoxyoxalyl chloride such as ethoxyoxalyl chloride, an aroyl chloride or bromide such as benzoyl or chlorobenzoyl chloride, an α-unsaturated-(3-6C)alkyl (2-20C)alkanoate such as isopropenyl stearate, a [(1-10C)acyloxy]chloromethane such as chloro(pivaloyloxy)methane, an aroyloxychloromethane such as benzoyloxychloromethane, a 1-[(1-10C)-alkoxy]carbonyloxy-1-chloro(1-6C)alkane such as 1-chloro-1-(ethoxycarbonyloxy)ethane, or a di-(1-6C)alkylaminocarbonyl chloride such as dimethylaminocarbonyl chloride.

The reaction may be performed under conventional N-acylation/alkylation conditions, for example in the presence of a base such as potassium carbonate or using the lithium, sodium or potassium salt of the compound of formula I wherein Rb and/or Rc is hydrogen and in a suitable solvent or diluent, for example 1,2-dimethoxyethane, di-n-butyl ethyl or diethyl ether, at a temperature in the range, for example 10°-80° C. However, when an α-unsaturated-(3-6C)alkyl (2-20C)alkanoate such as isopropenyl stearate is used, the process is preferably performed at an elevated temperature, for example at a temperature in the range, 120°-200° C., conveniently in the absence of solvent and in the presence of an acid catalyst such as p-toluenesulphonic acid.

When a sodium or potassium salt of a compound of formula I wherein Rb and/or Rc is hydrogen is used as starting material, this is conveniently formed in situ using sodium or potassium hydride in a non-aqueous solvent such as N,N-dimethylformamide or dimethyl sulphoxide at a temperature in the range, for example, 0°-30° C.

(b) For a derivative of formula I wherein Rb and/or Rc is an N-alkyl- or N-aralkylcarbamoyl radical, reacting a compound of formula I wherein Rb and/or Rc is hydrogen with an isocyanate of the formula Rd.NCO wherein Rd is hydrogen or an alkyl or aralkyl radical.

The reaction is conveniently performed in a suitable solvent or diluent, for example tetrahydrofuran, 1,2-dimethoxyethane or N,N-dimethylformamide, which should preferably be essentially anhydrous when Rd is other than hydrogen. However, when Rd is hydrogen, a convenient solvent is acetic acid which can also be used to generate the necessary cyanic acid in situ by addition of alkali-metal cyanate such as potassium cyanate. The process is usually carried out at a temperature in the range, for example, 10°-100° C.

It will be appreciated that in the above processes (a) and (b), depending on the amount of alkylating/acylating starting materials employed, it is possible to produce derivatives of formula I in which one or both Rb and Rc are other than hydrogen. Equally it will be appreciated that, it is in general possible to introduce different biodegradable radicals to Rb and Rc by a stepwise procedure as illustrated in the accompanying Examples.

A further process (c) according to the invention comprises hydrogenolysing a compound of the formula:

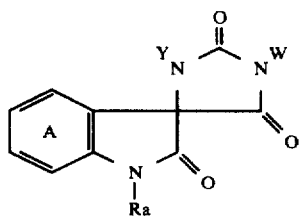

wherein one of Y and W is a non-toxic biodegradable protecting radical as defined hereinbefore other than a benzyloxycarbonyl or (benzyloxycarbonyloxy)alkyl radical, and the other of Y and W is a benzyloxycarbonyl radical.

The hydrogenolysis may be carried out under standard conditions well known in the art and which are compatible with the other functional groups in the molecule. Thus, for example, the process may be performed using a palladium metal catalyst, conveniently on an inert support such as carbon, using hydrogen at approximately atmospheric pressure at a temperature in the range, for example 10° to 40° C. and in an inert diluent or solvent such as 2-propanol, ethanol or 1,2-dimethoxyethane.

The starting materials of formula I wherein Rb and Rc are both hydrogen may be obtained using the following procedures:

(i) by the Bucherer-Bergs hydantoin synthesis by reacting an indolin-2,3-dione of the formula:

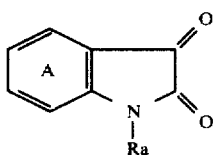

with an alkali metal cyanide such as sodium or potassium cyanide, and ammonium carbonate or carbamate, with or without intermediate isolation of a hydroxynitrile or amino-nitrile of the formula:

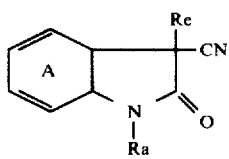

wherein Re is a hydroxy or amino radical.

The process is normally carried out in a suitable solvent such as methanol or ethanol and at a temperature in the range, for example, 20°–100° C.

The starting materials of formula IV may be obtained by conventional procedures of indole chemistry. For example, those compounds of formula I wherein Ra is other than a phenyl radical may be obtained by reacting an indoline-2,3-dione of formula IV wherein Ra is replaced by hydrogen with the appropriate alkyl or aralkyl chloride or bromide, in the presence of a base such as sodium or potassium hydroxide in dimethyl sulphoxide at a temperature of 20°–40° C.

Those starting materials of formula IV wherein Ra is a phenyl radical may be made, for example, by condensation of the appropriate diphenylamine with oxalyl chloride and aluminum chloride, as described in U.S. Pat. No. 3,509,149.

(ii) Reacting a compound of the formula:

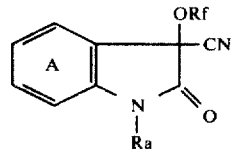

wherein Rf is an acetyl, propionyl, phenylsulphonyl, toluene p-sulphonyl, benzoyl radical or trimethylsilyl radical, with ammonium carbonate or carbamate.

Process (ii) is a modification of process (i) hereinabove and consequently similar reaction conditions may be used.

The starting materials of formula VI may be obtained by reacting a hydroxynitrile of formula V with acetyl, propionyl, phenylsulphonyl, toluene p-sulphonyl, benzoyl or trimethylsilyl chloride, in conventional manner.

Alternatively, those compounds of formula VI wherein Rf is a trimethylsilyl radical may be obtained by reaction of an appropriate indoline-2,3-dione with trimethylsilyl cyanide, at a temperature in the range, for example, 15°–40° C. and in a non-aqueous solvent, for example 1,2-dimethoxyethane.

(iii) For a compound of formula I wherein benzene ring A bears a nitro substituent and/or Ra is a benzyl radical bearing a nitro substituent, nitrating the corresponding compound of formula I in which benzene ring A and/or the radical Ra bear no more than two substituents.

The nitration may be carried out under conventional procedures, for example in the presence of sulphuric acid, using nitric acid at a temperature in the range, for example, 0° to 30° C., or using fuming nitric acid at a temperature in the range, for example −20° to 10° C.

(iv) For a compound of formula I wherein benzene ring A bears a chloro or bromo substituent, chlorinating or brominating the corresponding compound of formula I in which benzene ring A is unsubstituted.

The chlorination or bromination may be carried out using conventional procedures, for example using elemental chlorine or bromine optionally in the presence of a Friedel-Craft's catalyst such as ferric chloride, ferric bromide or iron powder, at a temperature in the range, for example 10° to 100° C. and in a suitable solvent or diluent, for example chloroform, nitrobenzene or acetic acid.

Alternatively, the chlorination or bromination may be carried out using sulphuryl chloride or bromide optionally in the presence of iodine as catalyst at a temperature in the range, for example 10° to 100° C., and in a suitable solvent or diluent, for example acetic acid or chloroform.

(v) For a compound of formula I wherein benzene ring A and/or Ra bears a hydroxy radical, dealkylating the corresponding compound of formula I wherein benzene ring A and/or Ra bears a (1–4C)alkoxy radical.

The dealkylation may be carried out using conventional procedures well known in the art, for example using a mixture of pyridine and hydrochloric or hydrobromic acid, at a temperature in the range for example 80° to 150° C.

When an optically active form of a derivative of formula I is required, one of the above processes (a)–(c)

may be performed using an optically active starting material.

The optically active forms of the starting materials of formula I wherein Rb and Rc are both hydrogen may be prepared by reacting the racemic form of such a compound with an optically-active form of a suitable organic base, for example of an N,N,N-trialkyl-(1-phenylethyl)ammonium hydroxide, followed by conventional separation of the diastereoisomeric mixture of salts or complexes thus obtained, and then liberation of the optically active form of said compound by conventional acidification procedure. This procedure is illustrated in preparation 57 hereinafter.

A preferred optically active compound of formula I wherein Rb and Rc are hydrogen which is a particularly potent inhibitor of aldose reductase is, for example, the (+) form 1'-(3,4-dichlorobenzyl)spiro[imidazoline-4,3'-indoline]-2,2',5-trione and nontoxic biodegradable derivatives thereof as defined hereinbefore are provided as a preferred feature of this invention.

The property of inhibiting the enzyme aldose reductase may be demonstrated in the following standard laboratory test. Thus, rats are made diabetic (as evidenced by severe glucosuria being present) by dosing with streptozotocin. The animals are then dosed daily with the test compound for at least 5 days. The animals are then killed and the eye lenses and sciatic nerves are removed. After a standard work-up procedure the residual sorbitol levels in each tissue are determined by gas liquid chromatography after conversion to the polytrimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

Alternatively, a modified test may be used in which the streptozotocin induced diabetic rats are dosed daily with test compound for two days. After 2-4 hours from the final dose the animals are killed and the sciatic nerves are removed and assessed for residual sorbitol levels as described above.

Preferred derivatives of formula I reduce residual sorbitol levels to levels which are similar to those of normal, undosed rats in either of these tests. However, in general the derivatives of formula I produce significant inhibition of the enzyme aldose reductase at an oral dose of 100 mg/kg or much less without any overt toxicity. Thus, by way of illustration, 1'-(3,4-dichlorobenzyl)-1-pivaloyloxymethyl-spiro-[imidazolidine-4,3'-indoline]-2,2', 5-trione produces a residual sobitol level in the sciatic nerve which is approximately 20% of that obtained in control undosed diabetic rats, following oral dosing at 12 mg/kg for 5 days.

When a derivative of the invention is used to produce an effect on the enzyme aldose reductase in warm-blooded animals, it may be administered primarily orally at a daily dose of 0.5 to 25 mg./kg., which is equivalent in man to a total daily dose in the range 10 to 750 mg. per man, given in divided doses if necessary.

The compounds of the invention may be administered in the form of pharmaceutical compositions and according to a further feature of the invention there is provided a pharmaceutical composition which comprises a derivative of formula I, together with a pharmaceutically acceptable diluent or carrier.

Especially preferred pharmaceutical compositions are those which are in a form suitable for oral administration, for example tablets, capsules, suspensions or solutions, which may be obtained by conventional methods and, if desired, may incorporate conventional diluents, carriers or other excipients. Other preferred compositions are those which are in a form suitable for parenteral administration, for example sterile injectable aqueous or non-aqueous solutions or suspensions, and for rectal administration, for example suppositories, and for topical administration to the eye, for example in the form of an ointment, gel or sterile solution buffered at an ophthalmically acceptable pH for example in the range pH 7.0-7.6. Dosage unit forms, for example tablets, capsules and suppositories, will generally contain from 10 mg. to 500 mg. of a derivative of formula I, depending on the form involved.

Solutions and ointments for topical administration to the eye will generally contain 0.02-20% by weight of a derivative of formula I.

The compositions of the invention may also contain one or more other agents which may have a useful effect in the treatment of diabetes or galactosemia, for example a hypoglycaemic agent such as tolbutamide, chlorpropamide, or glybenclamide.

The invention will now be illustrated in the following Preparations and non-limiting Examples in which, unless otherwise stated:

(i) all evaporations were carried out by rotary evaporation in vacuo (ii) all operations were carried out at room temperature, that is in the range 18°-26° C.;

(iii) petroleum ether (b.p. 60°-80° C.) is referred to as "petrol 60-80",and other petroleum ether fractions accordingly;

(iv) all compounds of formula I were fully characterised on the basis of microanalysis and NMR and IR spectroscopy:

(v) yields (where given) are for illustration and are not necessarily the maximum attainable; and Preparations 1-57 relate solely to the preparation of starting materials.

PREPARATION 1

A mixture of 1-(3,4-dichlorobenzyl)indoline-2,3-dione (12.0 g.), ammonium carbonate (36.0 g.) and potassium cyanide (5.2 g.) in methanol (300 ml.) and water (300 ml.) was heated under reflux at 95°-100° C. for 3 hours. The dark coloured solution obtained was cooled somewhat and decolourising charcoal (3.0 g. ) added. The mixture was then heated at 95°-100° C. and all the methanol allowed to distil out. The hot mixture was then separated by filtration and the residue washed with hot water. The filtrate and washings were combined, cooled and acidified with concentrated hydrochloric acid to pH 2. The buff solid which separated was collected, washed with water, air-dried and recrystallised twice from ethyl acetate/petrol 60-80 (4:1 v/v). There was thus obtained 1'-(3,4-dichlorobenzyl)-spiro[imidazolidine-4,3'-indoline]-2,2',5-trione (3.3 g.), m.p. 269°-271° C.

The starting material was obtained as follows:

An ethanol solution of potassium hydroxide (100 ml. of a 1 M solution) was added to a stirred solution of indoline-2,3-dione (isatin) (14.7 g.) in dimethyl sulphoxide (200 ml.). After 10 minutes a solution of 3,4-dichlorobenzyl chloride (21.5 g.) in dimethyl sulphoxide (10 ml.) was added. The mixture was stirred for 72 hours, and then poured into water (600 ml.). The solid which formed was collected, washed with water, air-dried and recrystallised from ethyl acetate/petrol 60-80

(3:2 v/v). There was thus obtained 1-(3,4-dichlorobenzyl)indoline-2,3-dione (13.8 g), m.p. 183°-184° C.

the starting material in Prep. I, using the appropriate isatin and halide of the formula Ra.X. The following properties and yields were obtained:

| Compound No. | X | Ra | Substituent on benzene ring A | m.p. (°C.) | Recrystallisation solvents (v/v) | Yield (%) |
| --- | --- | --- | --- | --- | --- | --- |
| 1 | Br | 4-bromo-2-fluorobenzyl | none | 151–153 | i-PrOH/Pet* (1:3) | 73 |
| 2 | Cl | naphth-1-ylmethyl | none | 172–174 | EtOAc/Pet* (1:3) | 54 |
| 3 | Br | n-propyl | 6-chloro | 118–120 | Petrol 80–100 | 57 |
| 4 | Cl | 3,4-dichlorobenzyl | 5-fluoro | 190–192 | EtOAc/Pet* (1:3) | 40 |

*petrol 60-80

PREPARATIONS 2-5

Using a similar procedure to that described in Prep. 1, but starting from the appropriate indoline-2,3-dione of formula IV, the following compounds of formula I were obtained:

| Prep. | Ra | Substituent on benzene ring A | m.p. (°C.) | Recrystallisation solvents (v/v) | Yield (%) |
| --- | --- | --- | --- | --- | --- |
| 2 | 4-bromo-2-fluorobenzyl | none | 298–300 | MeOH/EtOAc (1:3) | 19 |
| 3 | naphth-1-ylmethyl | none | 268–270 | i-PrOH/Pet* (1:3) | 25 |
| 4 | n-propyl | 6'-chloro | 261–263 | i-PrOH/Pet* (1:3) | 46 |
| 5 | 3,4-dichlorobenzyl | 5'-fluoro | 240–242 | EtOAc/Pet* (1:3) | 13 |

*petrol 60-80

The necessary starting materials of formula IV were obtained in an analogous manner to that described for

PREPARATIONS 6-33

Using a similar procedure to that described in Prep. 1, but starting from the appropriate indoline-2,3-dione of formula IV, the following compounds of formula I were obtained:

| Prep. | Ra | Substituent on benzene ring A | m.p. (°C.) | Recrystallisation solvent(s) | Yield+ (%) |
| --- | --- | --- | --- | --- | --- |
| 6 | 2,4-Cl$_2$—benzyl | none | 275–277 | i-PrOH/Pet* | 26 |
| 7 | n-nonyl | none | 134–136 | i-PrOH/H$_2$O | 20 |
| 8 | 4-Me—benzyl | none | 260–262 | MeOH | 40 |
| 9 | cinnamyl | none | 250–252 | i-PrOH/Pet | 43 |
| 10 | n-pentyl | none | 181–182 | EtOAc/Pet | 56 |
| 11 | n-hexyl | none | 164–166 | EtOAc/Pet | 60 |
| 12 | n-decyl | none | 156–157 | EtOAc/Pet | 10 |
| 13 | 3,4-Cl$_2$—benzyl | 5'-MeO | 245–247 | EtOAc/Pet | 24 |
| 14 | 3,4-Cl$_2$—benzyl | 5'-Me | 270–272 | Note (a) | 12 |
| 15 | 2F—4I—benzyl | none | 288–289 | MeOH | 32 |
| 16 | 3Cl—4Br—benzyl | none | 272–273 | MeOH | 30 |
| 17 | 3,4-Cl$_2$—benzyl | 5'-Cl | 270–272 | EtOAc/Pet | 21 |
| 18 | 3,4-Cl$_2$—benzyl | 7'-Cl | 239–240 | EtOAc/Pet | 42 |
| 19 | 2F—4Br—benzyl | 5'-Cl | 262–264 | EtOAc/Pet | 18 |
| 20 | 3,4-Cl$_2$—benzyl | 5'-Br | 208–210 | EtOAc/Pet | 7 |
| 21 | 3,4-Cl$_2$—benzyl | 7'-F | 243–244 | EtOAc/Pet | 12 |
| 22 | 4-Br—benzyl | none | 270–271 | DMF/H$_2$O | 8 |
| 23 | 2F—4Br—benzyl | 5'-F | 262–264 | EtOAc/Pet | 15 |
| 24 | 3,4-Cl$_2$—benzyl | 7'-Me | 237–238 | EtOAc/Pet | 18 |
| 25 | 3,4-(MeO)$_2$—benzyl | none | 270–271 | DMF/H$_2$O | 57 |
| 26 | 3-CF$_3$—benzyl | none | 276 | AcOH | 31 |
| 27 | 3,4-Cl$_2$—benzyl | 4'-Cl | 264–266 | EtOAc | 8 |
| 28 | 2-CN—benzyl | none | 248–250 | EtOAc/Pet | 47 |
| 29 | naphth-2-ylmethyl | none | 250–252 | i-PrOH/Pet | 20 |
| 30 | benzyl | 5'Br | 250–252 | EtOAc/Pet | 23 |
| 31 | 4-CN—benzyl | none | 282–283 | MeOH | 15 |
| 32 | 3,4-Cl$_2$—cinnamyl | none | 232–233 | EtOAc/Pet | 41 |

-continued

| Prep. | Ra | Substituent on benzene ring A | m.p. (°C.) | Recrystallisation solvent(s) | Yield+ (%) |
|---|---|---|---|---|---|
| 33 | phenyl | none | 257-259 | EtOAc/Pet | 16 |

*"Pet" stands for "petrol 60-80"
+Yields are of recrystallised product.
Note (a): purified by column chromatography on silica gel using 1:3 v/v ethyl acetate/toluene as eluant.

The necessary starting materials of formula IV were in general obtained in an analogous manner to that described for the starting material in Prep. 1, starting from the appropriate substituted indoline-2,3-dione and halide of the formula Ra.X, and had the following properties:

| Compound No. | X | Ra | Substituent on benzene ring A | m.p. (°C.) | Recrystallisation solvent(s) | Yield+ (%) |
|---|---|---|---|---|---|---|
| 1 | Cl | 2,4-Cl$_2$—benzyl | none | 189-190 | EtOAc | 64 |
| 2 | Br | n-nonyl | none | 43-45 | Pet* | 52 |
| 3 | Cl | 4-Me—benzyl | none | 141-143 | EtOAc/Pet | 56 |
| 4 | Br | cinnamyl | none | 137-139 | i-PrOH | 55 |
| 5 | Br | n-pentyl | none | 47-49 | Pet | 27 |
| 6 | Br | n-hexyl | none | 41-42 | Pet | 24 |
| 7 | Br | n-decyl | none | 54-56 | Pet | 38 |
| 8 | Cl | 3,4-Cl$_2$—benzyl | 5-MeO | 158-159 | Cyclohexane | 22 |
| 9 | Cl | 3,4-Cl$_2$—benzyl | 5-Me | 199-200 | i-PrOH | 61 |
| 10 | Br | 2F—4I—benzyl | none | 159-160 | MeOH | 28 |
| 11 | Br | 3Cl—4Br—benzyl | none | 188-189 | EtOH | 38 |
| 12 | Cl | 3,4-Cl$_2$—benzyl | 5-Cl | 171-172 | CCl$_4$ | 26 |
| 13 | Cl | 3,4-Cl$_2$—benzyl | 7-Cl | 175-176 | Pet/Toluene | 58 |
| 14 | Cl | 2F—4Br—benzyl | 5-Cl | 164-165 | i-PrOH | 48 |
| 15 | Cl | 3,4-Cl$_2$—benzyl | 5-Br | 164-166 | i-PrOH | 23 |
| 16 | Cl | 3,4-Cl$_2$—benzyl | 7-F | Note (a) | — | 77 |
| 17 | Br | 4-Br—benzyl | none | 184-186 | EtOAc | 53 |
| 18 | Br | 2F—4Br—benzyl | 5-F | 167-168 | i-PrOH | 62 |
| 19 | Cl | 3,4-Cl$_2$—benzyl | 7-Me | 184-186 | i-PrOH | 32 |
| 20 | Cl | 3,4-(MeO)$_2$—benzyl | none | 125-127 | i-PrOH | 33 |
| 21 | Cl | 3-CF$_3$—benzyl | none | 160-162 | i-PrOH | 68 |
| 22 | Cl | 3,4-Cl$_2$—benzyl | 4-Cl | 221-222 | i-PrOH | 53 |
| 23 | Br | 2-CN—benzyl | none | 165-167 | MeOH/i-PrOH | 72 |
| 24 | Br | naphth-2-ylmethyl | none | 174-176 | MeOH/DMF | 59 |
| 25 | Br | benzyl | 5-Br | 150-151 | MeOH/H$_2$O | 82 |
| 26 | Br | 4-CN—benzyl | none | 222-223 | Acetone | 46 |
| 27 | Cl | 3,4-Cl$_2$—cinnamyl | none | 194-196 | EtOAc | 55 |

*"Pet" stands for "petrol 60-80"
+Yields are of recrystallised product.
Note (a): isolated as a waxy solid, pure by TLC (SiO$_2$): 1/1 v/v EtOAc/Toluene).

1-Phenylindoline-2,3-dione (for Prep. 33) was obtained as a solid, m.p. 138°-139° C. (recrystallised from propan-2-ol) in 56% yield by the procedure of U.S. Pat. Ser. No. 3,509,149.

PREPARATION 34

Sulphuryl chloride (16.0 ml.) was added during 10 minutes to a stirred mixture of 1'-(3,4-dichlorobenzyl)-spiro[imidazolidine-4,3'-indoline]-2,2',5-trione (28.2 g.) in acetic acid (400 ml.). The mixture obtained was then stirred at 60°-65° C. for 40 minutes. The clear solution which formed was poured into water (3 l.). The solid which was precipitated was collected by filtration, washed with water and air-dried. Recrystallisation of the crude solid thus obtained from aqueous propan-2-ol gave 5'-chloro-1'-(3,4-dichlorobenzyl)-spiro[imidazolidine-4,3'-indoline]-2,2',5-trione (15.4 g.), m.p. 257°-259° C.

PREPARATIONS 35-37

Fuming nitric acid (0.2 ml.) was added during 10 minutes to a stirred solution of 1'-(3,4-dichlorobenzyl)-spiro[imidazolidine-4,3'-indoline]-2,2',5-trione (1.79 g.) in concentrated sulphuric acid (1.5 ml.) maintained at a temperature of 0°-5° C. The reaction mixture was then stirred at 0°-5° C. for 1 hour and finally at 5°-20° C. for a further 1 hour. The solution was then poured onto crushed ice (300 g.) and the mixture which formed was extracted with ethyl acetate. The combined extracts were washed with water (3×150 ml.) then with brine (100 ml.) and dried (MgSO$_4$). The extracts were evaporated and the residual oil was redissolved in ethyl acetate (20 ml.). The solution was evaporated on to chromatographic silica gel and the solid residue added to the top of a column of the same silica gel made up in toluene. The column was eluted with increasing concentrations of ethyl acetate in toluene (up to 1:1 v/v). The fractions containing the major component [TLC:Rf~0.6 on SiO₂:eluant 1:1 v/v EtOAc/toluene] were combined and evaporated. The residue was recrystallised from a mixture of toluene, ethyl acetate and petrol 60–80 to give 1'-(3,4-dichlorobenzyl)-5'-nitrospiro[imidazolidine-4,3'-indoline]-2,2',5-trione (Prep. 35) (0.46 g.), m.p. 249°–251° C.

Using a similar procedure, but starting from 1'-(4-bromo-2-fluorobenzyl)-spiro[imidazolidine-4,3'-indoline]-2,2',5-trione and 1'-benzyl-5'-bromospiro[imidazolidine-4,3'-indoline]-2,2',5-trione respectively there was obtained: 1'-(4-bromo-2-fluoro-5-nitrobenzyl)-5'-nitrospiro[imidazolidine-4,3'-indoline]-2,2',5-trione (Prep. 36), m.p. 180°–181° C. (recystallised from i-PrOH/petrol 60–80) in 36% yield; and 1'-(4-nitrobenzyl)-5'-bromo-7'-nitrospiro[imidazolidine-4,3'-indoline]-2,2',5-trione (Prep. 37), m.p. 245°–246° C. (recrystallised from EtOAc/petrol 60–80) in 7% yield.

PREPARATIONS 38–41

Trimethylsilyl cyanide (0.6 g.) was added to a stirred solution of 1-(4-bromo-3,5-dichlorobenzyl)indoline-2,3-dione (1.2 g.) in dry 1,2-dimethoxyethane (40 ml.). The mixture was stirred for 5 hours to give 1-(4-bromo-3,5-dichlorobenzyl)-3-cyano-3-(trimethylsilyloxy)indoline-2-one in situ. A solution of ammonium carbonate (6.0 g.) in water (40 ml.) was then added. The subsequent mixture was heated under reflux for 6 hours, cooled and evaporated. The residue was treated with water (100 ml.) and the mixture separated by filtration. The residue was washed with warm water (2×50 ml.). The aqueous filtrate and washings were cooled to 0°–5° C. and acidified to pH4 with 2 M hydrochloric acid. The solid which separated was collected by filtration, washed with water, air-dried and recrystallised from aqueous N,N-dimethylformamide (DMF) (1:1 v/v) to give 1'-(4-bromo-3,5-dichlorobenzyl)-spiro[imidazolidine-4,3'-indoline]-2,2',5-trione (Prep. 38) (0.63 g.), m.p. 290°–292° C.

Using a similar procedure, but starting from the appropriate 1-benzyl-indoline-2,3-dione there were obtained the following compounds:

(Prep. 39): 1'-(3,4-dichlorobenzyl)-6'-chlorospiro[imidazolidine-4,3'-indoline]-2,2',5-trione, m.p. 286°–287° C. (recrystallised from EtOAc/petrol 60–80) in 57% yield.

(Prep. 40): 1'-(3,4-dichlorobenzyl)-5',6'-dimethylspiro[imidazolidine-4,3'-indoline]-2,2',5-trione, m.p. 262°–263° C. (recrystallised from EtOAc/petrol 60–80) in 10% yield; and (Prep. 41): 1'-(3,4-dichlorobenzyl)-7'-ethylspiro[imidazolidine-4,3'-indoline]-2,2',5-trione, m.p. 232°–233° C. (recrystallised from EtOAc/petrol 60–80) in 7% yield.

The necessary starting materials of formula IV were obtained using a similar procedure to that described for the analogous starting material in Example I starting from the appropriate indoline-2,3-dione and halide of the formula RaX and had the following properties:

| Compound No. | X | Ra | Substituent(s) on benzene ring A | m.p. (°C.) | Recrystallisation solvent(s) | Yield (%) |
|---|---|---|---|---|---|---|
| 1 | Cl | 4-Br—3,5-Cl₂—benzyl | none | 241–243 | MeOH | 34 |
| 2 | Cl | 3,4-Cl₂—benzyl | 6-Cl | 180–182 | i-PrOH | 25 |
| 3 | Cl | 3,4-Cl₂—benzyl | 5,6-Me₂ | 218–220 | EtOAc | 31 |
| 4 | Cl | 3,4-Cl₂—benzyl | 7-Et | 124–126 | petrol 60–80 | 12 |

PREPARATIONS 42–48

Using a similar procedure to that described in Prep. 1, but starting from the appropriate 1-substituted indoline-2,3-dione of formula IV, the following compounds of formula I were obtained:

| Prep. | Ra | Substituent(s) on benzene ring A | m.p. (°C.) | Recrystallisation Solvents | Yield+ (%) |
|---|---|---|---|---|---|
| 42 | 4-Me—benzyl | 5'-Cl | 257–259 | EtOAc/pet* | 12 |
| 43 | methyl | 5'-Cl | 306–308 | Acetone/pet* | 25 |
| 44 | n-hexyl | 5'-Cl | 158–160 | EtOAc/pet* | 26 |
| 45 | 3,4-Cl₂—benzyl | 4',5'-Cl₂ | 155–156 (decomp) | EtOAc/pet* | 10 |
| 46 | 3,4-(MeO)₂—benzyl | 5'-Cl | 285–287 | EtOAc/pet* | 14 |
| 47 | 3,4-Cl₂—benzyl | 5'-Cl—7'-Me | 273–275 | EtOH/2-MeO—EtOH | 29 |
| 48 | 2-F—4-Br—benzyl | 5'-Cl—7'-Me | 247–249 | EtOAc/pet* | 25 |

+Yields are of recrystallised material
*"Pet" stands for "Petrol 60–80"

The necessary starting materials of formula IV were obtained in an analogous manner to that described for the starting material in Prep. 1 that is by reaction of the appropriate indoline-2,3-dione with a halide of the formula Ra.X, and had the following properties:

| Compound No. | X | Ra | Substituent(s) on benzene ring A | m.p. (°C.) | Recrystallisation Solvent(s) | Yield+ % |
|---|---|---|---|---|---|---|
| 1 | Br | 4-Me—benzyl | 5-Cl | 156–158 | i-PrOH | 52 |
| 2 | I | methyl | 5-Cl | 170–172 | i-PrOH | 60 |
| 3 | Br | n-hexyl | 5-Cl | 86–88 | i-PrOH | 49 |
| 4 | Cl | 3,4-Cl₂—benzyl | 4,5-Cl₂ | 185–187 | EtOAc/pet* | 71 |

| Compound No. | X | Ra | Substituent(s) on benzene ring A | m.p. (°C.) | Recrystal- lisation Solvent(s) | Yield+ % |
|---|---|---|---|---|---|---|
| 5 | Cl | 3,4-(MeO)₂—benzyl | 5-Cl | 162–164 | i-PrOH/DMF | 33 |
| 6 | Cl | 3,4-Cl₂—benzyl | 5-Cl—7-Me | 191–194 | MeCN/2-MeO—EtOH | 41 |
| 7 | Cl | 2-F—4-Br—benzyl | 5-Cl—7-Me | 179–182 | MeCN/2-MeO—EtOH | 43 |

+Yields are of recrystallised material
*"pet" stands for "petrol 60–80"

PREPARATION 49–53

Using a similar procedure to that described in Prep. 38, but starting from the appropriate 1-benzylindoline-2,3-dione of formula IV and with intermediate formation of the corresponding 1-benzyl-3-trimethylsilyloxy-3-cyano-indoline-2-one of the formula VI(Rf=trimethylsilyl), the following compounds of formula I may be obtained:

| Prep. | Ra | Substituent(s) on benzene ring A | m.p. (°C.) | Recrystallisation Solvent(s) | Yield+ (%) |
|---|---|---|---|---|---|
| 49 | 3,4-Cl₂—cinnamyl | 5'-Cl | 295–297 | DMF/H₂O | 16 |
| 50 | 4-HO—benzyl | none | 285–286 | MeOH | 52 |
| 51 | 3,4-Cl₂—benzyl | 5',6'-F₂ | 244–245 | EtOAc/petrol 80–100 | 11 |
| 52 | 3,4-Cl₂—benzyl | 5',6'-Cl₂ | 255–256 | EtOAc/petrol 60–80 | 8 |
| 53 | 3,5-Cl₂—benzyl | none | 237–238 | Toluene | 54 |

+Yields are of recrystallised material.

The necessary starting materials of formula IV were in general obtained in an analogous manner to that described for the starting material in Prep. 1. that is by reaction of the appropriate indoline-2,3-dione with a halide of the formula Ra.X, and had the following properties:

| Compound No | X | Ra | Substituent(s) on benzene ring A | m.p. (°C.) | Recrystal- lisation solvent(s) | Yield+ (%) |
|---|---|---|---|---|---|---|
| 1 | Cl | 3,4-Cl₂—cinnamyl | 5-Cl | 194–196 | EtOAc | 55 |
| 2 | Cl | 3,4-Cl₂—benzyl | 5,6-F₂ | 170–171 | Toluene | 5 |
| 3 | Cl | 3,4-Cl₂—benzyl | 5,6-Cl₂ | 197–200 | EtOAc/pet* | 70 |
| 4 | Cl | 3,5-Cl₂—benzyl | none | 192–193 | EtOH | 48 |

+Yields are of recrystallised material.
*"pet" stands for "petrol 60–80"

The compound 1-(4-hydroxybenzyl)indoline-2,3-dione required as starting material for Prep. 50 was obtained as follows:

An ethanol solution of potassium hydroxide (16.6 g. in 400 ml.) was added to a stirred solution of indoline-2,3-dione (isatin) (43.6 g.) in dimethyl sulphoxide (400 ml.). After 10 minutes a solution of 4-acetoxybenzyl bromide (76.3 g.) in dimethyl sulphoxide (40 ml.) was added. The mixture was stirred for 72 hours and then poured into ice/water (~1000 ml.). The gum which first formed slowly crystallised. The solid which formed was recrystallised from methanol (500 ml.) to give 1-(4-acetoxybenzyl)indoline-2,3-dione as a solid, m.p. 159°–161° C.

This solid, together with further material obtained from the mother liquors, was chromatographed on silica (500 g.) using toluene containing an increasing amount of ethyl acetate as eluant (up to 25% v/v). The fractions of eluate collected using eluant containing 20–25% v/v ethyl acetate were combined and evaporated to give 1-(4-hydroxybenzyl)indoline-2,3-dione as a low melting solid (m.p. 28°–35° C.) after recrystallisation from a mixture of toluene and ethyl acetate.

Note: It will be appreciated that the acetoxy group is hydrolysed to the required hydroxy group during the above chromatography on silica.

PREPARATION 54

A mixture of pyridine (20 ml.) and concentrated hydrochloric acid (20 ml.) was heated at about 180° C. for 20 minutes. 1'-(3,4-Dichlorobenzyl)-5'-methoxyspiro[imidazolidine-4,3'-indoline]-2,2',5-trione (2.0 g.) was then added and the subsequent mixture was further heated for 1 hour at about 180° C. The solution obtained was cooled and poured into water (200 ml.). The aqueous mixture was extracted with ethyl acetate (2×200 ml.). The combined extracts were washed with water (3×100 ml.), then with brine (saturated sodium chloride solution) (100 ml.), dried (MgSO₄) and evaporated. The resultant oil was dissolved in ethyl acetate (20 ml.) and evaporated onto chromatographic silica gel (10 g.), which was then added to the top of a column of the same silica gel (100 g.) made up in toluene. The column was then eluted with toluene containing an increasing concentration of ethyl acetate (up to 50% v/v). The fractions of eluate collected using eluant containing 50% v/v ethyl acetate were combined and evaporated to give 1'-(3,4-dichlorobenzyl)-5'-hydroxyspiro[imidazolidine-4,3'-indoline]-2,2',5-trione (0.7 g.), m.p. 296°–298° C. (after recrystallisation from ethyl acetate/petrol 60–80).

PREPARATION 55

A filtered solution of 1'-(3,4-dichlorobenzyl)-spiro[imidazolidine-4,3'-indoline]-2,2',5-trione (3.76 g.) in water (20 ml.) containing sodium hydroxide (0.40 g.) was evaporated, remaining traces of water being removed by azeotropic distillation with toluene. There was thus obtained the corresponding mono-sodium salt in quantitative yield as an amorphous hygroscopic solid having a satisfactory microanalysis.

PREPARATION 56

Sodium hydride (1.5 g., 50% w/w dispersion in mineral oil) was added continuously to a solution of spiro[imidazolidine-4,3'-indoline]-2,2',5-trione (2.17 g.) in N,N-dimethylformamide (40 ml.) and water (20 ml.). The resultant mixture was stirred for 30 minutes and then a solution of 3,4-dichlorobenzyl chloride (1.95 g.) in tetrahydrofuran (5 ml.) was added dropwise during 10 minutes. The solution obtained was stirred at room temperature for two hours and then poured into water (150 ml.). The mixture was acidified with concentrated hydrochloric acid and then extracted with ether (2×100 ml.). The combined extracts were washed with water (3×100 ml.), then with saturated sodium chloride solution (100 ml.), dried (MgSO$_4$) and evaporated. The residual solid was dissolved in chloroform and purified by chromatography on silica (25 g.) using an increasing concentration of ethyl acetate in cyclohexane as eluant. Evaporation of the ethyl acetate rich fractions gave 1'-(3,4-dichlorobenzyl)-spiro[imidazolidine-4,3'-indoline]-2,2',5-trione identical with that obtained in Prep. 1.

PREPARATION 57

(dl)-1'-(3,4-Dichlorobenzyl)-spiro[imidazolidine-4,3'-indoline]-2,2',5-trione (4.4 g.) was added to 61.5 ml of a 0.19 M solution of (l)-N,N,N-trimethyl(1-phenylethyl)ammonium hydroxide. The mixture was warmed to facilitate solution and then evaporated. The residue was dissolved in warm propan-2-ol (11 ml.). The solution obtained was cooled to 0° C. for 48 hours. The crystalline solid which formed was collected by filtration, washed with cold propan-2-ol (5 ml.), then with petrol 40–60 (20 ml.) and recrystallised twice from propan-2-ol to give the (d)-diastereoisomeric salt of (l)-N,N,N-trimethyl-(1-phenylethyl)ammonium hydroxide and (d)-1'-(3,4-dichlorobenzyl)-spiro[imidazolidine-4,3'-indoline]-2,2',5-trione (1.6 g.), m.p. 148°–150° C., [α]$_D^{23}$+32.8° (c, 1.4; MeOH).

The salt (1.6 g.) was dissolved in water (10 ml.) and methanol (3 ml.) and the solution acidified with concentrated hydrochloric acid (1 ml.). The precipitated solid was collected, washed with water and recrystallised from ethanol to give (d)-1'-(3,4-dichlorobenzyl)-spiro[imidazolidine-4,3'-indoline]-2,2',5-trione, m.p. 199°–200° C., [α]$_D^{23}$+41° (c, 1.6, MeOH).

The starting quaternary ammonium hydroxide solution was obtained by passing an aqueous solution (l)-N,N,N-trimethyl(1-phenylethyl)ammonium iodide (27.8 g.) (I. Angres and H. E. Zieger, *J.Org.chem.* 1975, 40, 1457–1460) down a column of anion exchanging resin ('Amberlite' IRA 401, 200 g.) newly converted into the hydroxide form ('Amberlite' is a trademark).

EXAMPLE 1

A solution of 1'-(3,4-dichlorobenzyl)-spiro[imidazolidine-4,3'-indoline]-2,2',5-trione (3.76 g.) in dry N,N-dimethylformamide (50 ml.) was stirred during the addition of sodium hydride (0.50 g.) [50% w/w dispersion in oil]. When the addition was complete, the solution was stirred until effervescence had ceased (about 1 hour). Chloromethyl pivalate (1.55 g.) was then added. The mixture was stirred for 18 hours and then poured into water (200 ml.). The aqueous mixture was carefully acidified by addition of concentrated hydrochloric acid and the precipitated material has extracted with ethyl acetate (2×150 ml.). The combined extracts were washed with water (3×100 ml.) and then with brine (1×150 ml.), dried (MgSO$_4$) and evaporated. The oil obtained was dissolved in ethyl acetate (100 ml.) and silica gel (10 g., type 7734 available from E. Merck Darmstadt, West Germany) was added. The mixture was evaporated and the residue was added to the top of a column of silica gel (150 g. Merck type 7734) made up in toluene. Elution with an increasing gradient of ethyl acetate in toluene with analysis by thin layer chromatography (SiO$_2$:50% ethyl acetate/toluene) of the fractions of eluate and combination and evaporation of those containing the major component (relative flow value: 0.6) gave 1'-(3,4-dichlorobenzyl)-1-pivaloyloxymethyl-spiro[imidazolidine-4,3'-indoline]-2,2',5-trione as a white solid (1.3 g.), m.p. 209°–211° C., after recrystallisation from a mixture of ethyl acetate and 60–80 petrol.

EXAMPLE 2

1'-(3,4-Dichlorobenzyl)-spiro[imidazolidine-4,3'-indoline]-2,2',5-trione (1.8 g.) was added to a solution of phosphorus oxychloride (0.55 ml.) in N,N-dimethylformamide (20 ml.) and the mixture was stirred at 60° C. for 90 minutes. The solution obtained was then poured into water (150 ml.). The solid which formed was collected by filtration, washed with water, air-dried and then recrystallised twice from ethyl acetate/petrol 60–80 to give 1'-(3,4-dichlorobenzyl)-3-formyl-spiro[imidazolidine-4,3'-indoline]-2,2',5-trione (0.6 g.), m.p. 244°–46° C.

EXAMPLE 3

Ethyl chloroformate (1.1 g.) was added to a stirred mixture of 1'-(3,4-dichlorobenzyl)-spiro[imidazolidine-4,3'-indoline]-2,2',5-trione (1.8 g.) and sodium carbonate (2.0 g.) in dimethoxyethane (60 ml.). The mixture was stirred at 25° C. for 16 hours. The solid was removed by filtration and the filtrate was evaporated. The residue obtained was recrystallised twice from ethyl acetate/petrol 60–80 to give 1'-(3,4-dichlorobenzyl)-1,3-di(ethoxycarbonyl)-spiro[imidazolidine-4,3'-indoline]-2,2',5-trione (0.6 g.), m.p. 180°–182° C.

EXAMPLE 4

A solution of ethyl chloroformate (0.55 g.) in 1,2-dimethoxyethane (20 ml.) was added dropwise to a stirred mixture of 1'-(3,4-dichlorobenzyl)-spiro[imidazolidine-4,3'-indoline]-2,2',5-trione (1.8 g.) and sodium carbonate (2.0 g.) in 1,2-dimethoxyethane (60 ml.). When the addition was completed, the mixture was stirred for 16 hours and then evaporated. The residual solid was dissolved in warm water (150 ml.) and the solution obtained was slowly acidified (concentrated hydrochloric acid). The solid which was precipitated was separated by filtration, washed with water, air-dried and recrystallised twice from propan-2-ol/petrol 60–80 to give 3-ethoxycarbonyl-1'-(3,4-dichlorobenzyl)-spiro[imidazolidine-4,3'-indoline]-2,2',5-trione (0.35 g.), m.p. 192°–194° C.

EXAMPLE 5

A solution of benzoyl chloride (0.63 g.) in 1,2-dimethoxyethane (10 ml.) was added dropwise to a stirred mixture of 1'-(3,4-dichlorobenzyl)-spiro[imidazolidine-4,3'-indoline]-2,2',5-trione (1.8 g.) and triethylamine (0.51 g.) in 1,2-dimethoxyethane (50 ml.) cooled at 0°–5° C. When the addition was completed, the solution was stirred at 20°–25° C. for three hours. Silica gel (5 g., Merck type 7734) was added to the solution and the mixture was evaporated. The residue obtained was added to the top of a column of silica gel (75 g., Merck type 7734) made up in toluene. The column was eluted with increasing concentration of ethyl acetate in toluene up to 25% v/v and the fractions containing the major product [Relative flow value: 0.4, on Merck SiO$_2$ TLC plates No. 5715; eluant: EtOAc/Toluene, 1:1 v/v] were collected, combined and evaporated. The solid thereby obtained was recrystallised from ethyl acetate/petrol 60–80 to give 3-benzoyl-1'-(3,4-dichlorobenzyl)-spiro[imidazolidine-4,3'-indoline]-2,2',5-trione (0.34 g.), m.p. 251°–253° C.

EXAMPLE 6

1'-(3,4-Dichlorobenzyl)-spiro[imidazolidine-4,3'-indoline]-2,2',5-trione (1.8 g.) was stirred in anhydrous N,N-dimethylformamide (50 ml.) under an atmosphere of nitrogen at 25° C. Sodium hydride (0.25 g; 50% w/v oil dispersion) was added, and the mixture stirred for 30 minutes. 3-Bromophthalide (1.15 g.) was then added. The mixture was stirred for 16 hours and then poured into water (150 ml.). The mixture was acidified (concentrated hydrochloric acid) and then extracted with ethyl acetate (150 ml.). The extract was washed with water (2×150 ml.), brine (150 ml.) and then dried (MgSO$_4$). The dry solution was evaporated onto silica gel (10 g., Merck type 7734) which was then added to the top of a column of silica gel (150 g., Merck type 7734) made up in toluene. The column was eluted with an increasing concentration of ethyl acetate in toluene up to 25% v/v. The fractions containing the major product [Relative flow value: 0.5 on Merck SiO$_2$ TLC plates No. 5715; eluant: EtOAc/toluene, 1:1 v/v] were collected and evaporated to give an oil which crystallised on treatment with ethyl acetate/petrol 60–80 to give 1'-(3,4-dichlorobenzyl)-3-phthalidyl-spiro[imidazolidine-4,3'-indoline]-2,2',5-trione (0.4 g.), m.p. 154°–158° C.

EXAMPLE 7

(All parts by weight)

A mixture of 1'-(3,4-dichlorobenzyl)-1-pivaloyloxymethyl-spiro[imidazolidine-4,3'-indoline]-2,2',5-trione (50 parts), lactose (27 parts) and maize starch (20 parts), was stirred thoroughly and a paste formed from maize starch (2 parts) and water (40 parts) was added and thoroughly mixed in. The resultant mass was passed through a 16 mesh screen, then dried at 60° C. and passed through a 20 mesh screen. Magnesium stearate (1 part) was added to the granules obtained, and the whole compressed by conventional means into tablets, containing 10, 20, 50 and 100 mg. of active ingredient and suitable for oral administration for therapeutic purposes.

EXAMPLE 8

A solution of benzyl chloroformate (7.6 g.) in 1,2 dimethoxyethane (50 ml.) was added dropwise to a stirred mixture of 1'-(3,4-dichlorobenzyl)-spiro[imidazolidine-4,3'-indoline]-2,2',5-trione (7.4 g.) and sodium carbonate (8 g.) in 1,2 dimethoxyethane (200 ml.). When the addition was completed the mixture was stirred for 72 hours and then evaporated. The residual solid was dissolved in warm water (300 ml.) and the solution obtained was carefully acidified (concentrated hydrochloric acid) and then extracted with ethyl acetate (3×150 ml.). The combined extracts were washed successively with water (2×200 ml.) and brine (1×200 ml.) and then dried (MgSO$_4$). Evaporation of the solvent gave a buff solid which was recrystallised from ethyl acetate/petrol 60–80 to give 3-benzyloxycarbonyl-1'-(3,4-dichlorobenzyl)-spiro[imidazolidine-4,3'-indoline]-2,2',5-trione (6.5 g.), m.p. 215°–217° C.

EXAMPLE 9

Ethyl chloroformate (0.6 g.) was added slowly to a stirred mixture of 3-benzyloxycarbonyl-1'-(3,4-dichlorobenzyl)-spiro[imidazolidine-4,3'-indoline]-2,2',5-trione (2.55 g.) and sodium carbonate (2.0 g.) in 1,2-dimethoxyethane (60 ml.). The mixture was stirred for 16 hours and the solid then removed by filtration. The filtrate was evaporated to give an oil which solidified on treatment with a few drops of ether. This solid was recrystallised from ethyl acetate/petrol 60–80 to give 3-benzyloxycarbonyl-1-ethoxycarbonyl-1'(3,4-dichlorobenzyl)-spiro[imidazolidine-4,3'-indoline]-2,2',5-trione (1.8 g.), m.p. 128°–131° C.

EXAMPLE 10

A mixture of 3-benzyloxycarbonyl-1-ethoxycarbonyl-1'-(3,4-dichlorobenzyl)spiro[imidazolidine-4,3'-indoline]-2,2',5-trione (1.7 g.), 10% w/w palladium on carbon (0.1 g.), acetic acid (0.3 ml.), ethanol (25 ml.) and 1,2-dimethoxyethane (50 ml.) was hydrogenated at atmospheric pressure for 2 hours. The mixture was separated by filtration through diatomaceous earth and the filtrate was evaporated. The residual oil solidified on treatment with a few drops of toluene. The solid obtained was recrystallised from ethyl acetate/petrol 60–80 to give 1-ethoxycarbonyl-1'-(3,4-dichlorobenzyl)-spiro[imidazolidine-4,3'-indoline]-2,2',5-trione (0.7 g.), 176°–179° C.

EXAMPLE 11

3-Benzyloxycarbonyl-1'-(3,4-dichlorobenzyl)-spiro[imidazolidine-4,3'-indoline]-2,2',5-trione (2.0 g.) was heated under reflux in freshly distilled acetic anhydride (20 ml.) for 3 hours and then evaporated. The residual oil obtained, solidified on treatment with a few drops of ether to give a solid which was recrystallised from ethyl acetate/petrol 60–80. There was thus obtained 1-acetyl-3-benzyloxycarbonyl-1'-(3,4-dichlorobenzyl)-spiro[imidazolidine-4,3'-indoline]-2,2',5-trione (1.8 g.), m.p. 159°–161° C.

EXAMPLE 12

Using a similar procedure to that described in Example 10, but starting from 1-acetyl-3-benzyloxycarbonyl-1'-(3,4-dichlorobenzyl)-spiro[imidazolidine-4,3'-indoline]-2,2',5-trione (1.8 g.) there was obtained 1-acetyl-1'-(3,4-dichlorobenzyl)-spiro[imidazolidine-4,3'-indoline]-2,2',5-trione (0.7 g.), m.p. 185°-187° C. after recrystallisation from ethylacetate.

EXAMPLE 13

A solution of ethoxyoxalyl chloride (0.7 g.) in 1,2-dimethoxyethane (30 ml.) was added dropwise to a solution of 1'-(3,4-dichlorobenzyl)-spiro[imidazolidine-4,3'-indoline]-2,2',5-trione (1.85 g.) and triethylamine (0.50 g.) in 1,2-dimethoxyethane (50 ml.) cooled to 0° C. When the addition was complete, the reaction mixture was allowed to warm up and stirred at ambient temperature for 3 hours. Chromatographic silica gel (5 g.) was then added and the mixture was evaporated. The residue was added to the top of a column of chromatographic silica gel (150 g.) made up in toluene. The column was eluted, with an increasing gradient of ethyl acetate in toluene with analysis of the eluted fractions by thin layer chromatography (SiO$_2$:50% EtOAc/toluene). Those fractions of eluate containing the major component (relative flow value 0.6) were combined and evaporated to give 1'-(3,4-dichlorobenzyl)-3-ethoxyoxalyl-spiro[imidazolidine-4,3'-indoline]-2,2',5-trione as a white solid (0.25 g.), m.p. 247°-249° C. after recrystallisation from ethyl acetate/petrol 60-80.

EXAMPLE 14

Ethanolic potassium hydroxide solution (1 M; 5.2 ml) was added to a solution of 1'-(4-bromo-2-fluorobenzyl)-spiro-[imidazolidine-4,3'-indoline]-2,2',5-trione (2.0 g.) in dimethyl sulphoxide (10 ml.). The solution was stirred for 5 minutes and then chloromethyl pivalate (0.75 g.) was slowly added. After the addition was completed, the reaction mixture was further stirred for 16 hours; and then poured into water (100 ml.). The aqueous mixture was carefully acidified (concentrated hydrochloric acid). The precipitate which formed was washed with water, air dried and recrystallised twice from 2-propanol to give 1'-(4-bromo-2-fluorobenzyl)-1-(pivaloyloxymethyl)-spiro[imidazolidine-4,3'-indoline]-2,2',5-trione, as a white solid (0.75 g.), m.p. 220°-222° C.

EXAMPLE 15

Using a similar procedure to that described in Example 14, but starting from (+)-1'-(3,4-dichlorobenzyl)-spiro[imidazolidine-4,3'-indoline]-2,2',5-trione (0.94 g.) there was obtained (+)-1'-(3,4-dichlorobenzyl)-1-(pivaloyloxymethyl)-spiro[imidazolidine-4,3'-indoline]-2,2',5-trione as an oil (0.3 g.), [α]$_D^{23}$+23.8 (c. 1.0; EtOH), NMR (90 MHz; d$_6$DMSO): 1.2 [9H,s, (CH$_3$)$_3$C]; 5.03 (2H,s, CH$_2$); 5.5 (2H,s, NCH$_2$O.CO); 7.0-7.8 (7H, multiplet, aromatic H); 9.35 (1H,s, NH); m/e 489 (Cl$^{35}$), after chromatography of the crude product on silica gel using an increasing gradient of ethyl acetate in toluene (as described for Example 13).

EXAMPLE 16

Using a similar procedure to that described in Example 14, but starting from 1'-(3,4-dichlorobenzyl)-7'-fluoro-spiro[imidazolidine-4,3'-indoline]-2,2',5-trione (1.97 g), there was obtained 1'-(3,4-dichlorobenzyl)-7'-fluoro-1-(pivaloyloxymethyl)-spiro[imidazolidine-4,3'-indoline]-2,2',5-trione as a foam (0.6 g.), NMR (90 MHz, d$_6$DMSO): δ1.2 [9H,s, (CH$_3$)$_3$C]; 5.1 (2H, s, CH$_2$); 5.5 (2H, s, NCH$_2$O.CO.); 7.1-7.7 (6H,multiplet aromatic H); 9.35 (1H, s, NH); m/e 507 (Cl$^{35}$), after chromatography of the crude product on silica gel using an increasing gradient of ethyl acetate in toluene (as described in Example 13).

EXAMPLE 17

Using a similar procedure to that described in Example 7, but using 1'-(3,4-dichlorobenzyl)-7'-fluoro-1-pivaloyloxymethyl-spiro[imidazolidine-4,3'-indoline]-2,2',5-trione or another derivative of formula I described in Examples 2-6 or 8-15 as active ingredient, there may be obtained tablets containing 10, 20, 50 or 100 mg. of active ingredient, suitable for oral administration for therapeutic purposes.

What is claimed is:

1. A non-toxic biodegradable derivative of 1'-substituted-spiro[imidazolidine-4,3'-indoline]-2,2',5-trione, said derivative having the formula:

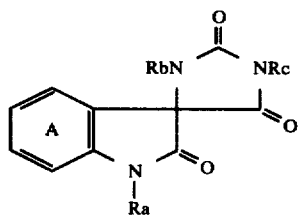

wherein Ra is a (1-12 C)alkyl radical, a phenyl naphthylmethyl or cinnamyl radical, the aromatic rings of which optionally bear one or two halogeno radicals, or Ra is a benzyl radical optionally bearing one, two or three substituents independently selected from halogeno trifluoromethyl, (1-4 C)alkyl, (1-4 C)alkoxy, nitro, cyano and hydroxy radicals; Rb and Rc are independently selected from hydrogen and non-toxic biodegradable protecting radicals, but are not both hydrogen; and benzene ring A optionally bears one substituent selected from halogeno, (1-4 C)alkyl, (1-4 C)alkoxy, nitro and hydroxy radicals, or bears two substituents independently selected from halogeno, (1-4 C)alkyl and nitro radicals.

2. A derivative as claimed in claim 1 wherein Ra is a methyl, ethyl, propyl, butyl, pentyl, hexyl, nonyl or decyl radical, a phenyl, naphthylmethyl or cinnamyl radical, the aromatic rings of which optionally bear one or two fluoro, chloro, bromo or iodo radicals, or Ra is a benzyl radical optionally bearing one, two or three substituents independently selected from fluoro, chloro, bromo, iodo, trifluoromethyl, methyl, ethyl, methoxy, ethoxy, nitro, cyano and hydroxy radicals; and benzene ring A optionally bears one substituent selected from fluoro, chloro, bromo, iodo, methyl, ethyl, methoxy, ethoxy, nitro and hydroxy radicals, or bears two substituents independently selected from fluoro, chloro, bromo, iodo, methyl, ethyl and nitro radicals.

3. A derivative as claimed in claim 1 wherein Ra is a methyl, n-propyl, n-hexyl, n-nonyl, n-decyl, phenyl, cinnamyl, 3,4-dichlorocinnamyl, naphth-1-ylmethyl, naphth-2-ylmethyl, benzyl, 3,4-dichlorobenzyl, 4-bromo-2-fluorobenzyl, 4-methylbenzyl, 2-fluoro-4-iodobenzyl, 4-bromo-3-chlorobenzyl, 4-chlorobenzyl, 4-bromobenzyl, 3,4-dimethoxybenzyl, 3-(trifluoromethyl)benzyl, 2-cyanobenzyl, 4-cyanobenzyl, 4-bromo-2-fluoro-5-nitrobenzyl, 4-nitrobenzyl, 4-bromo-3,5-dichlorobenzyl, 2,4-dichlorobenzyl, 4-hydroxybenzyl or 3,5-dichlorobenzyl radical; and benzene ring A is unsubstituted or bears 4'-chloro, 5'-fluoro, 5'-chloro, 5'-bromo, 5'-methyl, 5'-methoxy, 5'hydroxy, 5'-nitro, 6'-chloro, 7'-fluoro, 7'-chloro, 7'-methyl, 7'-ethyl, 5',6'-difluoro, 5',6'-dichloro, 4',5'-dichloro, 5',6'-dimethyl, 5'-bromo-7'-nitro or 5'-chloro-7'-methyl substituents.

4. A derivative as claimed in claim 1 wherein Ra is a 4-bromo-2-fluorobenzyl, 4-bromo-3-chlorobenzyl, 3,4-dichlorobenzyl or 2-fluoro-4-iodobenzyl radical; and benzene ring A is unsubstituted or bears a halogeno substituent located at position 5', 6' or 7'.

5. A derivative as claimed in claim 1 wherein Rb and Rc are independently selected from hydrogen, acyl and 1-(acyloxy)alkyl radicals, in which the acyl is an alkanoyl, optionally substituted aroyl, alkoxycarbonyl, optionally substituted aralkoxycarbonyl or an alkoxyoxalyl radical; and from N-alkylcarbamoyl, N,N-dialkylcarbamoyl, optionally substituted N-arylcarbamoyl, optionally substituted N-aralkylcarbamoyl and optionally substituted phthalidyl radicals; but Rb and Rc are not both hydrogen.

6. A derivative as claimed in claim 1 wherein Rb and Rc are independently selected from (2–12 C)alkanoyl, benzoyl [optionally bearing a halogeno, (1–4 C)alkyl or cyano substituent], (1–10 C)alkoxycarbonyl, benzyloxycarbonyl (optionally bearing a halogeno substituent), 1-[(2–20 C)alkanoyl]oxy-(1–6 C)alkyl, [(1–10 C)alkoxy]oxalyl, 1-(benzoyloxy)-(1–6 C)alkyl [optionally bearing a halogeno, (1–4 C)alkyl or cyano nuclear substituent], 1-[(1–10 C)alkoxycarbonyloxy]-(1–6 C)alkyl, N-(1–6 C)alkylcarbamoyl, N,N-di-(1–6 C)alkylcarbamoyl, N-phenyl- or N-benzylcarbamoyl [optionally bearing a (1–4 C)alkyl or (1–4 C)alkoxy nuclear substituent], or a phthalidyl radical [optionally bearing a (1–4 C)alkyl, (1–4 C)alkoxy or halogeno substituent]; but Rb and Rc are not both hydrogen.

7. A derivative as claimed in claim 1 wherein Rb and Rc are independently selected from acetyl, pivaloyl, butyryl, stearoyl, benzoyl, methylbenzoyl, chlorobenzoyl, cyanobenzoyl, ethoxycarbonyl, t-butoxycarbonyl, benzyloxycarbonyl, chlorobenzyloxycarbonyl, pivaloyloxymethyl, stearoyloxymethyl, 1-(pivaloyloxy)ethyl, methoxyoxalyl, ethoxyoxalyl, benzoyloxymethyl, (chlorobenzoyl)oxymethyl, (methylbenzoyl)oxymethyl, (methoxybenzoyl)oxymethyl, (cyanobenzoyl)oxymethyl, (ethoxycarbonyl)oxymethyl, 1-(ethoxycarbonyloxy)ethyl, N-methylcarbamoyl, N,N-dimethylcarbamoyl, N-phenylcarbamoyl, N-(methoxyphenyl)carbamoyl, N-benzylcarbamoyl, N-(methylbenzyl)carbamoyl, or a phthalidyl radical optionally bearing a fluoro, chloro, bromo, methyl or methoxy substituent.

8. A derivative as claimed in claim 1 wherein Ra is a benzyl radical bearing one or two halogeno radicals, Rb and Rc are independently selected from hydrogen and alkoxycarbonyl, aralkoxycarbonyl, alkoxyoxalyl and 1-[alkoxycarbonyloxy]alkyl radicals, but are not both hydrogen, and benzene ring A is unsubstituted or bears a halogeno substituent located at position 5', 6' or 7'.

9. A non-toxic biodegradable derivative as claimed in claim 1 which is a derivative of an aldose reductase inhibitor selected from:

1'-(3,4-dichlorobenzyl)-spiro[imidazolidine-4,3'-indoline]-2,2',5-trione,
1'-(4-bromo-2-fluorobenzyl)-spiro[imidazolidine-4,3'-indoline]-2,2',5-trione,
1'-(3,4-dichlorobenzyl)-5'-fluorospiro[imidazolidine-4,3'-indoline]-2,2',5-trione,
1'-(4-bromo-3-chlorobenzyl)-spiro[imidazolidine-4,3'-indoline]-2,2',5-trione,
5'-chloro-1'-(3,4-dichlorobenzyl)spiro[imidazolidine-4,3'-indoline]-2,2,',5-trione,
1'-(4-bromo-2-fluorobenzyl)-5'-chloro-spiro[imidazolidine-4,3'-indoline]-2,2,',5-trione,
5'-bromo-1'-(3,4-dichlorobenzyl)-spiro[imidazolidine-4,3'-indoline]-2,2',5-trione,
1'-(4-bromo-2-fluorobenzyl)-5'-fluoro-spiro[imidazolidine-4,3'-indoline]-2,2',5-trione,
1'-(3,4-dichlorobenzyl)-5',6'-dichloro-spiro[imidazolidine-4,3'-indoline]-2,2',5-trione,
1'-(3,4-dichlorobenzyl)-5',6'-difluoro-spiro[imidazolidine-4,3'-indoline]-2,2',5-trione and
1'-(2-fluoro-4-iodobenzyl)-spiro[imidazolidine-4,3'-indoline]-2,2',5-trione, said derivative being one wherein one or both of the imidazolidine nitrogen atoms bears a non-toxic biodegradable protecting radical.

10. A compound selected from 1'-(3,4-dichlorobenzyl)-1-(pivaloyloxymethyl)-spiro[imidazolidine-4,3'-indoline]-2,2',5-trione, 1'-(4-bromo-2-fluorobenzyl)-1-(pivaloyloxymethyl)-spiro[imidazolidine-4,3'-indoline]-2,2',5-trione and 1'-(3,4-dichlorobenzyl)-7'-fluoro-1-(pivaloyloxymethyl)-spiro[imidazolidine-4,3'-indoline]-2,2',5-trione.

11. A pharmaceutical composition which comprises as active ingredient a non-toxic biodegradable derivative having the formula I as claimed in claim 1 together with a pharmaceutically acceptable diluent or carrier.

12. A method of inhibiting the enzyme aldose reductase which comprises administering to a warm-blooded animal requiring such treatment an aldose reductase inhibitory amount of a non-toxic biodegradable derivative having the formula I as claimed in claim 1.

* * * * *